US008536314B2

(12) United States Patent
Eggert et al.

(10) Patent No.: US 8,536,314 B2
(45) Date of Patent: Sep. 17, 2013

(54) FLUORESCENT PROTEINS, THEIR PRODUCTION AND USE

(75) Inventors: Thorsten Eggert, Essen (DE); Sascha Hausmann, Düsseldorf (DE); Michael Puls, Köln (DE)

(73) Assignee: Evocatal GmbH, Dusseldorf (DE)

( * ) Notice: Subject to any disclaimer, the term of this patent is extended or adjusted under 35 U.S.C. 154(b) by 113 days.

(21) Appl. No.: 12/783,301

(22) Filed: May 19, 2010

(65) Prior Publication Data

US 2010/0304435 A1 Dec. 2, 2010

(30) Foreign Application Priority Data

May 19, 2009 (DE) .......... 10 2009 021 990
Jun. 5, 2009 (DE) .......... 10 2009 024 281

(51) Int. Cl.
*C12N 15/01* (2006.01)
*A61K 38/00* (2006.01)

(52) U.S. Cl.
USPC ........ 530/402; 530/387.3; 530/350; 530/300; 530/400; 424/9.34; 424/9.6

(58) Field of Classification Search
None
See application file for complete search history.

(56) References Cited

U.S. PATENT DOCUMENTS

2006/0172940 A1* 8/2006 Kim et al. .......... 514/12

FOREIGN PATENT DOCUMENTS

DE 102005048828 A1 4/2007

OTHER PUBLICATIONS

SEQ Align (2012) sequence alignment of instant SEQ ID No:2, pp. 1 and 2.*
Christie et al. (20120 Structural Tuning of the Fluorescent Protein iLOV for Improved Photostability, J. Biol. Chem., vol. 287, No. 26, pp. 22295-22304.*
The attached SEQ Align for Eggert C53A and E12D (2012) p. 1-2.*
The attached "SEQ Align for instant SEQ 4" (2012) p. 1-2.*
Chapman et al., "The photoreversible fluorescent protein iL0V outperforms GFP as a reporter of plant virus infection", Proceedings of the National Academy of Sciences of the United States of America (2008), Volume: 105, Issue: 50, Publisher: National Academy of Sciences, pp. 20038-20043.
Drepper et al., "Reporter proteins for in vivo fluorescence without oxygen", Nature Biotechnology, Apr. 2007. vol. 25, No. 4, pp. 443-445.
"Synthetic construct FMN-based fluorescence protein gene, partial cds", Internet Research on Nov. 5, 2011 on the website of the National Center for Biotechnology Information, 2 pages, <http://www.ncbi.nim.nih.gov/nuccore/126023749>.
"Synthetic construnt FMN-based fluorescence protein gene partiai cds", Sequence Comparison on Nov. 5, 2009 1 page, <http://blast.ncbi.nlm.nih.gov/Blast.cgi>.
Kang et al., "Comparison of green fluorescent protein expression in two industrial *Escherichia coli* strains, BL21 and W3110, under co-expression of bacterial hemoglobin" Internet Research on Nov. 5, 2011 (Abstract), <http://www.springerlink.com/content/qt6d0hgewdfled2y/>, 1 page.
Na'Imatulapidah Abdul Majid et al., "Evaluation of Green Fluorescence Protein Selectable Marker for Oil Palm Transformation via Transient Expression", Asian Pacific Journal of Molecular Biology & Biotechnology, vol. 15, No. 1, pp. 1-8, <http://www.msmbb.org.my/apjmbb/html151/151a.pdf>.
Search Report (Recherchebricht), German Application No. 10 2000 024 281.3, dated Nov. 5, 2009, 4 pages.
Search Report (Europaischer Tellrecherchenbericht), EP1016679, dated Jul. 23, 2010, 4 pages.

* cited by examiner

*Primary Examiner* — Karen Cochrane Carlson
*Assistant Examiner* — Samuel Liu
(74) *Attorney, Agent, or Firm* — Senniger Powers LLP

(57) ABSTRACT

The present invention provides variants of fluorescent proteins, which are improved with regard to their properties for use as reporter proteins and/or in analytics. In particular, variants of fluorescent proteins are provided, which fluoresce brighter, show improved quantum yield and/or have shifted excitation or emission spectra. The fluorescent proteins according to the invention comprise in their LOV domain besides the substitution of a cysteine with an amino acid that does not covalently bind FMN at least one further point mutation.

7 Claims, 8 Drawing Sheets

FIG. 7

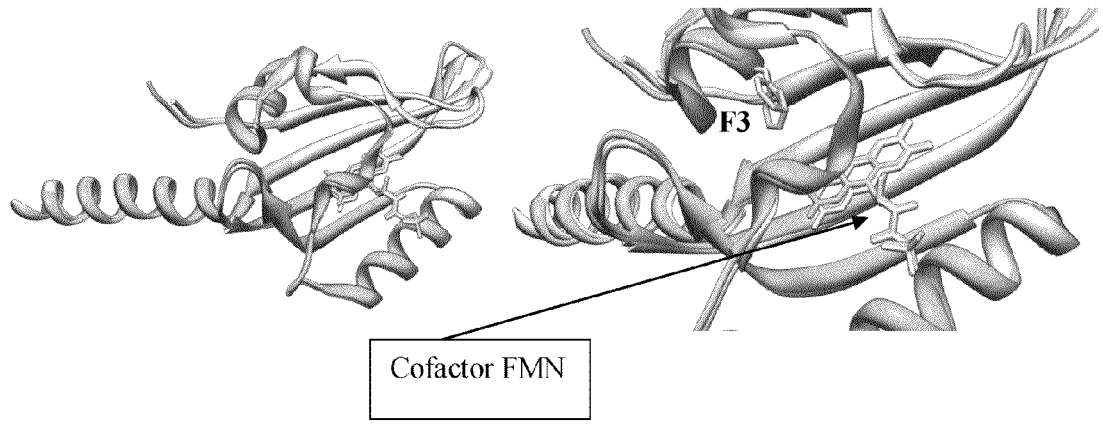

Cofactor FMN

FIG. 8

|          | 10                                     | 20                     | 30                  | 40      |
|----------|----------------------------------------|------------------------|---------------------|---------|
| evoglow Bs1 | MASFQSFGIPGQLEVIKKALDHVRVGVVITDPALEDNPIV |
| evoglow Bs2 | MASFQSFGIPGQLEVIKKALDHVRVGVVITDPALEDNPIV |
| evoglow Pp1 | - - - - - - - - - MINAKLLQLMVEHSNDGIVVAEQEGNESILI |
| Consensus   |                    H           GV           H |

|          | 50           | 60            | 70             | 80       |
|----------|--------------|---------------|----------------|----------|
| evoglow Bs1 | YVNQGFVQMTGYETEEILGKNARFLQGKHTDPAEVDNIRT |
| evoglow Bs2 | YVNQGFVQMTGYETEEILGKNARFLQGKHTDPAEVDNIRT |
| evoglow Pp1 | YVNPAFERLTGYCADDILYQDARFLQGEDHDQPGIAIIRE |
| Consensus   | YVN   F  TGY      IL  ARFLQG   D         IR |

(H)            (H)   (H) (F) (H)

|          | 90          | 100          | 110          | 120       |
|----------|-------------|--------------|--------------|-----------|
| evoglow Bs1 | ALQNKEPVTVQIQNYKKDGTMFWNELNIDP - -MEIEDKTY |
| evoglow Bs2 | ALQNKEPVTVQIQNYKKDGTMFWNELNIDP - -MEIEDKTY |
| evoglow Pp1 | AIREGRPCCQVLRNYRKDGSLFWNELSITPVHNEADQLTY |
| Consensus   | A    P       NY KDG  FWNEL  I P      E    TY |

(F)

|          | 130          | 140          | 150          | 160       |
|----------|--------------|--------------|--------------|-----------|
| evoglow Bs1 | FVGIQNDITKQKEYEKLLEDSLTEITALSTPIVPIRNGIS |
| evoglow Bs2 | FVGIQNDITKQKEYEKLLEHHHHHH - - - - - - - - - - - - - |
| evoglow Pp1 | YIGIQRDVTAQVFAEERVRELEAEVAELRRQQGQAKH - - - |
| Consensus   |    GIQ  D T  Q    E                      |

| | T30 | N37 | F46 | N61 | C62 | R63 | Q66 | V75 | I78 | R79 | L82 | N94 | N104 | L106 | I108 | F119 | V120 | G121 | Q123 |
|---|---|---|---|---|---|---|---|---|---|---|---|---|---|---|---|---|---|---|---|
| N1 | | | | | × | | | | | | | | | | | | | | |
| C2 | | | | | × | | × | | | | | × | | | | | | | |
| O2 | | | | | ×O | | | | | | | ×O | | | | | | | |
| N3 | | | | | × | | | | | | | ×O | | | | | | | |
| C4 | | | | | × | | | | | | | × | × | Δ | | | | | |
| O4 | | | × | | × | | | | | | | | O | | | | | | × |
| C4A | | | | | ×Δ | | | | | | | | | | | | | | |
| N5 | | | | | × | | | | | | | | | × | | | | | O |
| C5A | | | | | ×Δ | | | | | | | | | | Δ | | | | |
| C6 | | | | | | | | | | | | | | | | | | | × |
| C7 | | | | | | | | | | | | | | | Δ | | | | |
| C7M | Δ | | | | | | | | | | | | | | | ×Δ | Δ | ×Δ | |
| C8 | | | | | | | | | | | | | | | Δ | | | | |
| C8M | × | × | | | | | | | | | Δ | | | | Δ | | | | |
| C9 | | | | | | | | | | | | | | | Δ | | | | |
| C9A | | | | | ×Δ | | | | | | | | | | Δ | | | | |
| N10 | | | | | × | | | | | | | | | | | | | | |
| C10 | | | | | ×Δ | | | | | | | | | Δ | | | | | |
| C1' | | | | | | | | | Δ | | | | | | | | | | |
| C2' | | | | × | × | | | | | | | | | | | | | | |
| O2' | | | | × | × | | | | | | | | | | | | | | |
| C3' | | | | × | | | | | | | | | | | | | | | |
| O3' | | | | | | | | | × | | × | | | | | | | | |
| C4' | | | | | | | | | Δ | | | | | | | | | | |
| O4' | | | | | × | ×O | × | | | | | | | | | | | | |
| C5' | | | | | | | ×Δ | | | | | ×Δ | | | | | | | |
| O5' | | | | | | | | | | | | | | | | | | | |
| P | | | | | × | | | | | × | | | | | | | | | |
| O1P | | | | | ×O | | | | | | | | | | | | | | |
| O2P | | | | | ×O | | | | | | | | | | | | | | |
| O3P | | | | | | | | | × | ×O | | | | | | | | | |

SEQUENCE LISTING

```
<160> NUMBER OF SEQ ID NOS: 14

<210> SEQ ID NO 1
<211> LENGTH: 261
<212> TYPE: PRT
<213> ORGANISM: Bacillus subtilis

<400> SEQUENCE: 1

Met Ala Ser Phe Gln Ser Phe Gly Ile Pro Gly Gln Leu Glu Val Ile
1               5                   10                  15

Lys Lys Ala Leu Asp His Val Arg Val Gly Val Val Ile Thr Asp Pro
            20                  25                  30

Ala Leu Glu Asp Asn Pro Ile Val Tyr Val Asn Gln Gly Phe Val Gln
        35                  40                  45

Met Thr Gly Tyr Glu Thr Glu Glu Ile Leu Gly Lys Asn Ala Arg Phe
    50                  55                  60

Leu Gln Gly Lys His Thr Asp Pro Ala Glu Val Asp Asn Ile Arg Thr
65                  70                  75                  80

Ala Leu Gln Asn Lys Glu Pro Val Thr Val Gln Ile Gln Asn Tyr Lys
                85                  90                  95

Lys Asp Gly Thr Met Phe Trp Asn Glu Leu Asn Ile Asp Pro Met Glu
            100                 105                 110

Ile Glu Asp Lys Thr Tyr Phe Val Gly Ile Gln Asn Asp Ile Thr Lys
        115                 120                 125

Gln Lys Glu Tyr Glu Lys Leu Leu Glu Asp Ser Leu Thr Glu Ile Thr
    130                 135                 140

Ala Leu Ser Thr Pro Ile Val Pro Ile Arg Asn Gly Ile Ser Ala Leu
145                 150                 155                 160
```

```
Pro Leu Val Gly Asn Leu Thr Glu Glu Arg Phe Asn Ser Ile Val Cys
            165                 170                 175

Thr Leu Thr Asn Ile Leu Ser Thr Ser Lys Asp Asp Tyr Leu Ile Ile
        180                 185                 190

Asp Leu Ser Gly Leu Ala Gln Val Asn Glu Gln Thr Ala Asp Gln Ile
        195                 200                 205

Phe Lys Leu Ser His Leu Leu Lys Leu Thr Gly Thr Glu Leu Ile Ile
        210                 215                 220

Thr Gly Ile Lys Pro Glu Leu Ala Met Lys Met Asn Lys Leu Asp Ala
225                 230                 235                 240

Asn Phe Ser Ser Leu Lys Thr Tyr Ser Asn Val Lys Asp Ala Val Lys
            245                 250                 255

Val Leu Pro Ile Met
            260

<210> SEQ ID NO 2
<211> LENGTH: 137
<212> TYPE: PRT
<213> ORGANISM: Bacillus subtilis

<400> SEQUENCE: 2

Met Ala Ser Phe Gln Ser Phe Gly Ile Pro Gly Gln Leu Glu Val Ile
1               5                   10                  15

Lys Lys Ala Leu Asp His Val Arg Val Gly Val Val Ile Thr Asp Pro
            20                  25                  30

Ala Leu Glu Asp Asn Pro Ile Val Tyr Val Asn Gln Gly Phe Val Gln
        35                  40                  45

Met Thr Gly Tyr Glu Thr Glu Glu Ile Leu Gly Lys Asn Ala Arg Phe
    50                  55                  60

Leu Gln Gly Lys His Thr Asp Pro Ala Glu Val Asp Asn Ile Arg Thr
65                  70                  75                  80

Ala Leu Gln Asn Lys Glu Pro Val Thr Val Gln Ile Gln Asn Tyr Lys
            85                  90                  95

Lys Asp Gly Thr Met Phe Trp Asn Glu Leu Asn Ile Asp Pro Met Glu
        100                 105                 110

Ile Glu Asp Lys Thr Tyr Phe Val Gly Ile Gln Asn Asp Ile Thr Lys
        115                 120                 125

Gln Lys Glu Tyr Glu Lys Leu Leu Glu
    130                 135

<210> SEQ ID NO 3
<211> LENGTH: 142
<212> TYPE: PRT
<213> ORGANISM: Pseudomonas putida

<400> SEQUENCE: 3

Met Ile Asn Ala Gln Leu Leu Gln Ser Met Val Asp Ala Ser Asn Asp
1               5                   10                  15

Gly Ile Val Val Ala Glu Lys Glu Gly Asp Asp Thr Ile Leu Ile Tyr
            20                  25                  30

Val Asn Ala Ala Phe Glu Tyr Leu Thr Gly Tyr Ser Arg Asp Glu Ile
        35                  40                  45

Leu Tyr Gln Asp Ala Arg Phe Leu Gln Gly Asp Asp Arg Asp Gln Leu
    50                  55                  60

Gly Arg Ala Arg Ile Arg Lys Ala Met Ala Glu Gly Arg Pro Cys Arg
65                  70                  75                  80

Glu Val Leu Arg Asn Tyr Arg Lys Asp Gly Ser Ala Phe Trp Asn Glu
```

```
                    85                  90                  95
Leu Ser Ile Thr Pro Val Lys Ser Asp Phe Asp Gln Arg Thr Tyr Phe
                100                 105                 110

Ile Gly Ile Gln Lys Asp Val Ser Arg Gln Val Glu Leu Glu Arg Glu
            115                 120                 125

Leu Ala Glu Leu Arg Ala Arg Pro Lys Pro Asp Glu Arg Ala
        130                 135                 140

<210> SEQ ID NO 4
<211> LENGTH: 148
<212> TYPE: PRT
<213> ORGANISM: Pseudomonas putida

<400> SEQUENCE: 4

Met Ile Asn Ala Lys Leu Leu Gln Leu Met Val Glu His Ser Asn Asp
1               5                   10                  15

Gly Ile Val Val Ala Glu Gln Glu Gly Asn Glu Ser Ile Leu Ile Tyr
            20                  25                  30

Val Asn Pro Ala Phe Glu Arg Leu Thr Gly Tyr Cys Ala Asp Asp Ile
        35                  40                  45

Leu Tyr Gln Asp Ala Arg Phe Leu Gln Gly Glu Asp His Asp Gln Pro
    50                  55                  60

Gly Ile Ala Ile Ile Arg Glu Ala Ile Arg Glu Gly Arg Pro Cys Cys
65                  70                  75                  80

Gln Val Leu Arg Asn Tyr Arg Lys Asp Gly Ser Leu Phe Trp Asn Glu
                85                  90                  95

Leu Ser Ile Thr Pro Val His Asn Glu Ala Asp Gln Leu Thr Tyr Tyr
                100                 105                 110

Ile Gly Ile Gln Arg Asp Val Thr Ala Gln Val Phe Ala Glu Glu Arg
            115                 120                 125

Val Arg Glu Leu Glu Ala Glu Val Ala Glu Leu Arg Arg Gln Gln Gly
        130                 135                 140

Gln Ala Lys His
145

<210> SEQ ID NO 5
<211> LENGTH: 447
<212> TYPE: DNA
<213> ORGANISM: Pseudomonas putida

<400> SEQUENCE: 5
atgatcaacg caaaactcct gcaactgatg gtcgaacatt ccaacgatgg catcgttgtc      60
gccgagcagg aaggcaatga gagcatcctt atctacgtca acccggcctt cgagcgcctg     120
accggctact gcgccgacga tattctctat caggacgccc gctttcttca gggcgaggat     180
cacgaccagc cgggcatcgc aattatccgc gaggcgatcc gcgaaggccg ccctgctgc      240 caggtgctgc gcaactaccg caaagacggc agcctgttct ggaacgagtt gtccatcaca     300
ccggtgcaca acgaggcgga ccagctgacc taccacatcg gcatccagcg cgatgtcaca     360
gcgcaagtat tcgccgagga aagggttcgc gagctggagg ctgaagtggc ggaactgcgc     420
cggcagcagg gccaggccaa gcactga                                        447

<210> SEQ ID NO 6
<211> LENGTH: 447
<212> TYPE: DNA
<213> ORGANISM: Pseudomonas putida

<400> SEQUENCE: 6
```

```
atgatcaacg caaaactcct gcaactgatg gtcgaacatt ccaacgatgg catcgttgtc    60
gccgagcagg aaggcaatga gagcgtcctt atctacgtca acccggcctt cgagcgcctg   120
accggctact gcgccgacga tattctctat caggacgccc gttttcttca gggcgaggat   180
cacgaccagc cgggcatcgc aattatccgc gaggcgatcc gcgaaggccg ccctgctgc    240 caggtgctgc gcaactaccg caaagacggc ggcctgttct ggaacgagtt gtccatcaca   300
ccggtgcaca acgaggcgga ccagctgacc tacttcatcg gcatccagcg cgatgtcaca   360
gcgcaagtat tcgccgagga aagggttcgc gagctggagg ctgaagtggc gggactgcgc   420
cggcagcagg gccaggccaa gcactga                                       447
```

<210> SEQ ID NO 7
<211> LENGTH: 447
<212> TYPE: DNA
<213> ORGANISM: Pseudomonas putida

<400> SEQUENCE: 7

```
atgatcaacg caaaactccc gcaactgatg gtcgaacatt ccaacgatgg catcgttgtc    60
gccgagcagg aaggcaatga gagcatcctt atctacgtca acccggcctt cgagcgcctg   120
accggctact gcgccgacga tattctctat caggacgccc gttttcttca gggcgaggat   180
cacgaccagc cgggcatcgc aattatccgc gaggcgatcc gcgaaggccg ccctgctgc    240 caggtgctgc gcaactaccg caaagacggc agcctgttct ggaacgagtt gtccatcaca   300
ccggtgcaca acgaggcgga ccagctgact tactacatcg gcatccagcg cgatgtcaca   360
gcgcaagtac tcgccgagga aagggttcgc gagctggagg ctgaagtggc ggaactgcgc   420
cggcagcagg gccaggccaa gcactga                                       447
```

<210> SEQ ID NO 8
<211> LENGTH: 447
<212> TYPE: DNA
<213> ORGANISM: Pseudomonas putida

<400> SEQUENCE: 8

```
atgatcaacg caaaactcct gcaactgatg gtcgaacatt ccaacgatgg catcgttgtc    60
gccgaacagg aaggctatga gagcatcctt atctacgtca acccggcctt cgagcgcctg   120
accggctact gcgccgacga tattctctat caggacgccc gttttcttca gggcgaggat   180
cacgaccagc cgggcatcgc aattatccgc gaggcgatcc gcgaaggccg ccctgctgc    240 caggtgctgc gcaactaccg caaagacggc agcctgttct ggaacgagtt gtccatcaca   300
ccggtgcaca acgaggcgga ccagctgacc tactacatcg gcatccagcg cgatgtcaca   360
gcgcaagtat tcgccgagga aagggttcgc gagctggagg ctgaagtggc ggaactgcgc   420
cggcagcagg gccaggccaa gcactga                                       447
```

<210> SEQ ID NO 9
<211> LENGTH: 447
<212> TYPE: DNA
<213> ORGANISM: Pseudomonas putida

<400> SEQUENCE: 9

```
atgatcaacg caaaactcct gcaactgatg gtcgaacatt ccaacgatgg catcgttgtc    60
gccgagcagg aaggcaatga gagcatcctt atctatgtca acccggcctt cgagcgcctg   120
accggctact gcgccgacga tactctctat caggacgccc gttttcttca gggcgaggat   180
tacgaccagc cgggcatcgc aattatccgc gaggcgatcc gcgaaggccg ccctgctgc    240
```

| caggtgctgc gcaactaccg caaagacggc agcctgttct ggaacgagtt gtccatcaca | 300 |
| ccggtgcaca acgaggcgga ccagctgacc tactacatcg gcatccagcg cgatgtcaca | 360 |
| gcgcaagtat tcgccgagga aagggttcgc gagctggagg ctgaagtggc ggaactgcgc | 420 |
| cggcagcagg gccaggccaa gcactga | 447 |

```
<210> SEQ ID NO 10
<211> LENGTH: 447
<212> TYPE: DNA
<213> ORGANISM: Pseudomonas putida

<400> SEQUENCE: 10
```

| atgatcaacg caaaactcct gcaactgatg gtcgaacatt ccaacgatgg catcgttgtc | 60 |
| gccgagcagg aaggcaatga gagcatcctt atctacgtca acccggcctt cgagcgcctg | 120 |
| accggcttct gcgccgacga tattctctat caggacgccc gttttcttca gggcgaggat | 180 |
| cacgaccagc cggcatcgc aattatccgc gaggcgatcc gcgaaggccg cccctgctgc | 240 |
| caggtgctgc gcaactaccg caaagacggc agcctgttct ggaacgagtt gtccatcaca | 300 |
| ccggtgcaca acgaggcgga ccagctgacc tactacatcg gcatccagcg cgatgtcaca | 360 |
| gcgcaagtat tcgccgagga aagggttcgc gagctggagg ctgaagtggc ggaactgcgc | 420 |
| cggcagcagg gccaggccaa gcactga | 447 |

```
<210> SEQ ID NO 11
<211> LENGTH: 447
<212> TYPE: DNA
<213> ORGANISM: Pseudomonas putida

<400> SEQUENCE: 11
```

| atgatcaacg caaaactcct gcaactgatg gtcgaacatt ccaacgatgg catcgttgtc | 60 |
| gccgagcagg aaggcaatga gagcatcctt atctacgtca acccggcctt cgagcgcctg | 120 |
| accggctact gcgccgacga tattctctat caggacgccc gttttcttca gggcgaggat | 180 |
| cacgaccagc cggcatcgc aattatccgc gaggcgatcc gcgaaggccg cccctgctgc | 240 |
| caggtgctgc gcaactaccg caaagacggc agcctgttct ggaacgagtt gtccatcaca | 300 |
| ccggtgcaca acgaggcgga ccagctgacc tactgcatcg gcatccagcg cgatgtcaca | 360 |
| gcgcaagtat tcgccgagga aagggttcgc gagctggagg ctgaagtggc ggaactgcgc | 420 |
| cggcagcagg gccaggccaa gcactga | 447 |

```
<210> SEQ ID NO 12
<211> LENGTH: 447
<212> TYPE: DNA
<213> ORGANISM: Pseudomonas putida

<400> SEQUENCE: 12
```

| atgatcaacg caaaactcct gcaactgatg gtcgaccatt ccaacgatgg catcgttgtc | 60 |
| gccgagcagg aaggcaatga gagcatcctt atctacgtca acccggcctt cgagcgcctg | 120 |
| accggctact gcgccgacga tattctctat caggacgccc gtttccttca gggcgaggat | 180 |
| tacgaccagc cgggtatcgc aattatccgc gaggcgatcc gcgaaggccg cccctgctgc | 240 |
| caggtgctgc gcaactaccg caaagacggc agcctgttct ggaacgagtt gtccatcaca | 300 |
| ccggtgcaca acgaggcgga ccagctgacc tacttcatcg gcatccagcg cgatgtcaca | 360 |
| gcgcaagtat tcgccgagga aagggttcgc gagctggagg ctgaagtggc ggaactgcgc | 420 |
| cggcagctgg gccaggccaa gcactga | 447 |

<210> SEQ ID NO 13
<211> LENGTH: 447
<212> TYPE: DNA
<213> ORGANISM: Pseudomonas putida

<400> SEQUENCE: 13

```
atgatcaacg caaaactcct gcaactgatg gtcgaacatt ccaacgatgg catcgttgtc      60
gccaagcagg aaggcaatga gagcatcctt atctacgtca acccggcctt cgagcgcctg     120
accggctact gcgccgacga tattctctat caggacgccc gttttcttca gggcgaggat     180
cacgaccagc cgggcatcgc aattatccgc ggggcgatcc gcgaaggccg ccctgctgc      240 caggtgctgc gcaactaccg cagtgacggc agcctgttct ggaatgagtt gtccatcaca     300
ccggtgcaca acgaggcgga ccaggtgacc tactacatcg catcctgcg cgatgtcaca      360 gcgcaagtat tcgccgagga aagggttcgc gagctggagg ctgaagtggc ggagctgcgc     420
cggcagcagg gccaggccaa gcactga                                          447
```

<210> SEQ ID NO 14
<211> LENGTH: 447
<212> TYPE: DNA
<213> ORGANISM: Pseudomonas putida

<400> SEQUENCE: 14

```
atgatcaacg caaaactcct gcaactgatg gtcgaacatt ccaacgatgg catcgttgtc      60
gccgagcagg aaggcaatga gagcatcctt atctacgtca acccgacctt cgagcgcctg     120
accggctact gcgccgacga tattctctat caggacgccc gttttcttca tggcgaggat     180
cacgaccagc cgggcatcgc aattatccgc gaggcgatcc gcgaaggccg ccctgctgc      240 caggtgctgc gcaactaccg caaagacggc agcctgttct ggatcgagtt gtccatcaca     300
ccggtgcaca acgaggcgga ccagctgacc tactacatcg catccagcg cgatgtcaca      360 gcgcaagtat ttgccgagga aagggttcgc gagctggagg ctgaagtggc ggaactgcgc     420
cggcagcagg gccaggccaa gcactga                                          447
```

US 8,536,314 B2

FLUORESCENT PROTEINS, THEIR PRODUCTION AND USE

CROSS-REFERENCE TO RELATED APPLICATIONS

This application claims priority to German applications DE 10 2009 021 990.0 filed May 19, 2009, and DE 10 2009 024 281.3 filed Jun. 5, 2009, the entire disclosures of which are incorporated herein by reference.

FIELD OF THE INVENTION

The present invention relates to improved fluorescent proteins, their production and use.

BACKGROUND OF THE INVENTION

Fluorescent proteins are used for working on different analytical problems. Besides the so-called "green fluorescent protein" (GFP) and its derivatives and other fluorescent proteins, the fluorescence of which is based on the intrinsic formation of a chromophore by chemical modification of amino acids present in the primary structure, fluorescent proteins based on modified blue light receptor proteins have been described (Drepper, T., Eggert, T., Circolone, F., Heck, A., Krauβ, U., Guterl, J.-K., Wendorff, M., Losi, A., Gartner, W., Jaeger, K.-E. (2007). Reporter proteins for in vivo fluorescence without oxygen. Nature Biotech. 25, 443-445). In these proteins, which are described in German Patent Application DE 10 2005 048 828 A1, due to a point mutation the photocycle of the cofactor flavin mononucleotide (FMN) present in these proteins is interrupted, and the absorbed energy of the incident light is emitted by fluorescence. The sequence parts responsible for fluorescence in fluorescent proteins are referred to as LOV domains (light, oxygen, voltage domains). This form of fluorescent proteins is sold by the company evocatal GmbH under the product name EVOGLOW®. In the EVOGLOW® product series a distinction is made between fluorescent proteins obtained from different organisms. For example, fluorescent proteins obtained from *Bacillus subtilis* are designated EVOGLOW®-Bs, and fluorescent proteins obtained from *Pseudomonas putida* are designated EVOGLOW®-Pp. The sequences for three of these fluorescent proteins, namely EVOGLOW® Bs1, Bs2 and Pp1 are designated as sequence numbers 1, 2 and 4, respectively, in the sequence listing.

Fluorescent proteins can be used as so-called reporter proteins in cells or organisms to observe biochemical processes. Application areas are for example the investigation of gene-regulatory mechanisms or the monitoring of biotechnological processes. For application of the fluorescent proteins in extremophilic organisms, the reporter proteins have to be adapted with regard to stability against denaturing at harsh temperature and pH conditions in order to be able to detect a fluorescence signal. Furthermore, in certain investigations such as for example in colocalization studies of proteins it is necessary to be able to visualize two different populations of reporter proteins in the same cell. This is primarily achieved by different excitation and/or emission properties (colors) of the jointly used fluorescent proteins. The fluorescent proteins described in the literature thus far all have due to their identical chromophore FMN a comparable excitation and emission spectrum, as a result of which differentiation of the proteins is not possible.

SUMMARY OF THE INVENTION

It is therefore an object of the present invention to provide variants of fluorescent proteins, which are improved with regard to their properties for use as reporter protein and/or in analytics. Among them are, for example, brighter variants with improved quantum yield and/or shifted excitation or emission spectrum as compared to EVOGLOW® Bs-1 (sequence 1), Bs-2 (sequence 2), Pp-2 (sequence 3) or Pp-1 (sequence 4) fluorescent proteins, which contain a single mutation in the LOV domain where cysteine is replaced by alanine.

This object is solved by a fluorescent protein having an LOV domain in which at least one cysteine is replaced by another amino acid, preferably alanine, that does not covalently bind FMN, said fluorescent protein being characterized in that the LOV domain comprises besides the substitution of the at least one cysteine at least one further point mutation for improving the fluorescence intensity, photostability and/or for changing the fluorescence wavelength.

Briefly, therefore, the invention is directed to a fluorescent protein having an LOV domain in which at least one cysteine is replaced by another amino acid that does not covalently bind FMN, characterized in that the LOV domain comprises besides the substitution of the at least one cysteine at least one further point mutation for improving the fluorescence intensity, photostability and/or for changing the fluorescence wavelength.

In another aspect the invention is directed to an LOV domain in which at least one cysteine is replaced by another amino acid that does not covalently bind FMN, characterized in that said LOV domain comprises besides the substitution of the at least one cysteine at least one further point mutation for improving the fluorescence intensity, photostability and/or for changing the fluorescence wavelength.

In another aspect the invention is directed to a DNA molecule characterized in that it encodes the foregoing fluorescent protein or the foregoing LOV domain.

The invention is also directed to a method for producing a fluorescent protein having an LOV domain in which at least one cysteine is replaced by another amino acid, preferably alanine, that does not covalently bind FMN, said fluorescent protein being characterized in that the LOV domain comprises besides the substitution of the at least one cysteine at least one further point mutation for improving the fluorescence intensity, photostability and/or for changing the fluorescence wavelength, wherein a plasmid comprising a DNA sequence encoding the fluorescent protein is introduced into an organism and is expressed therein.

Other objects and features will be in part apparent and in part pointed out herein.

contained in the data sets was accentuated. The structures were visualized with UCSF Chimera.

Figure 3:
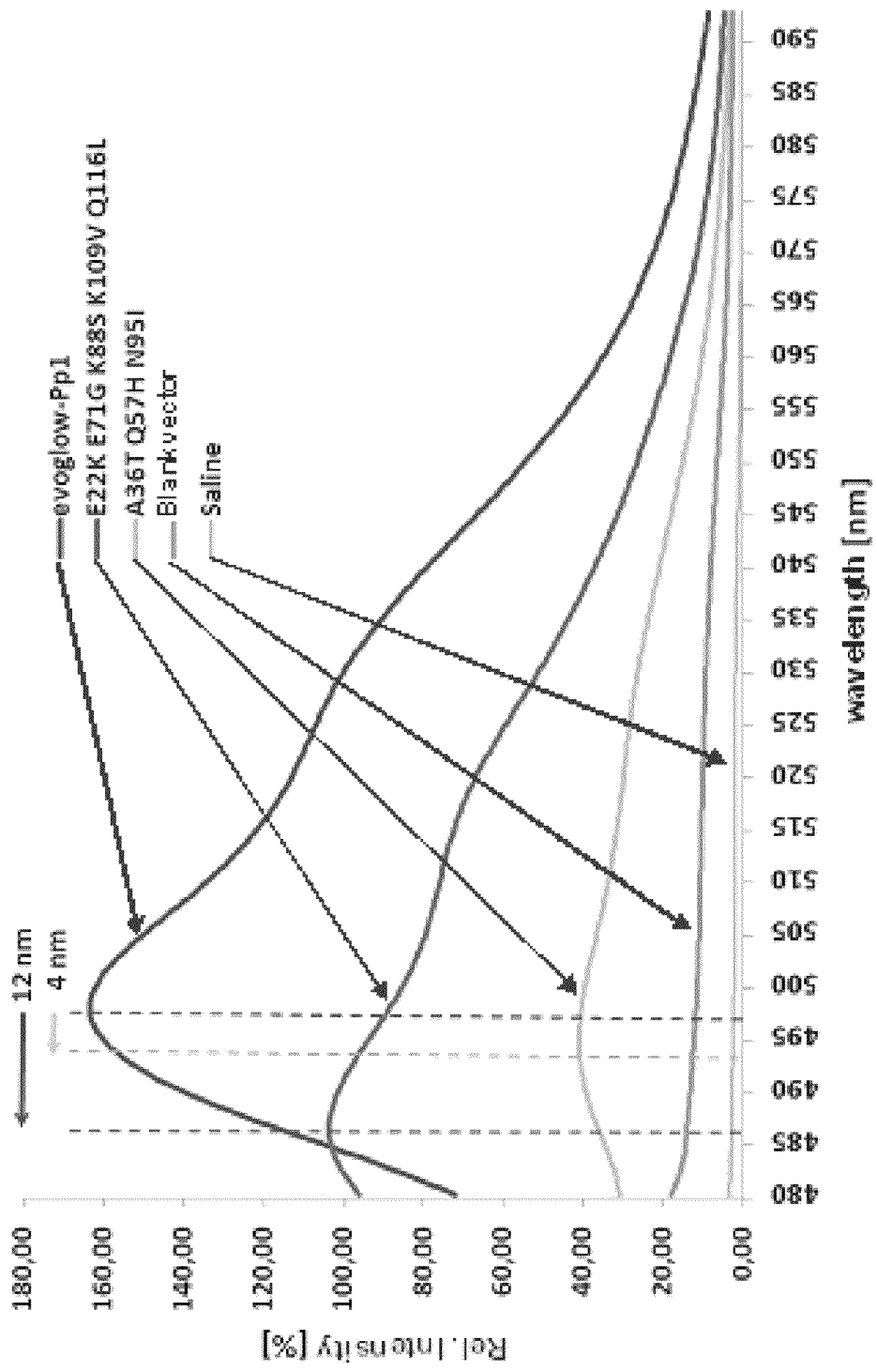

FIG. 3: Emission fluorescence spectra of cultures, which express EVOGLOW®-Pp1 and identified variants with different emission maximums. The cultures were washed with saline and adjusted to a cell density corresponding to an $O.D._{580\,nm}$ of 0.5.

Figure 4:
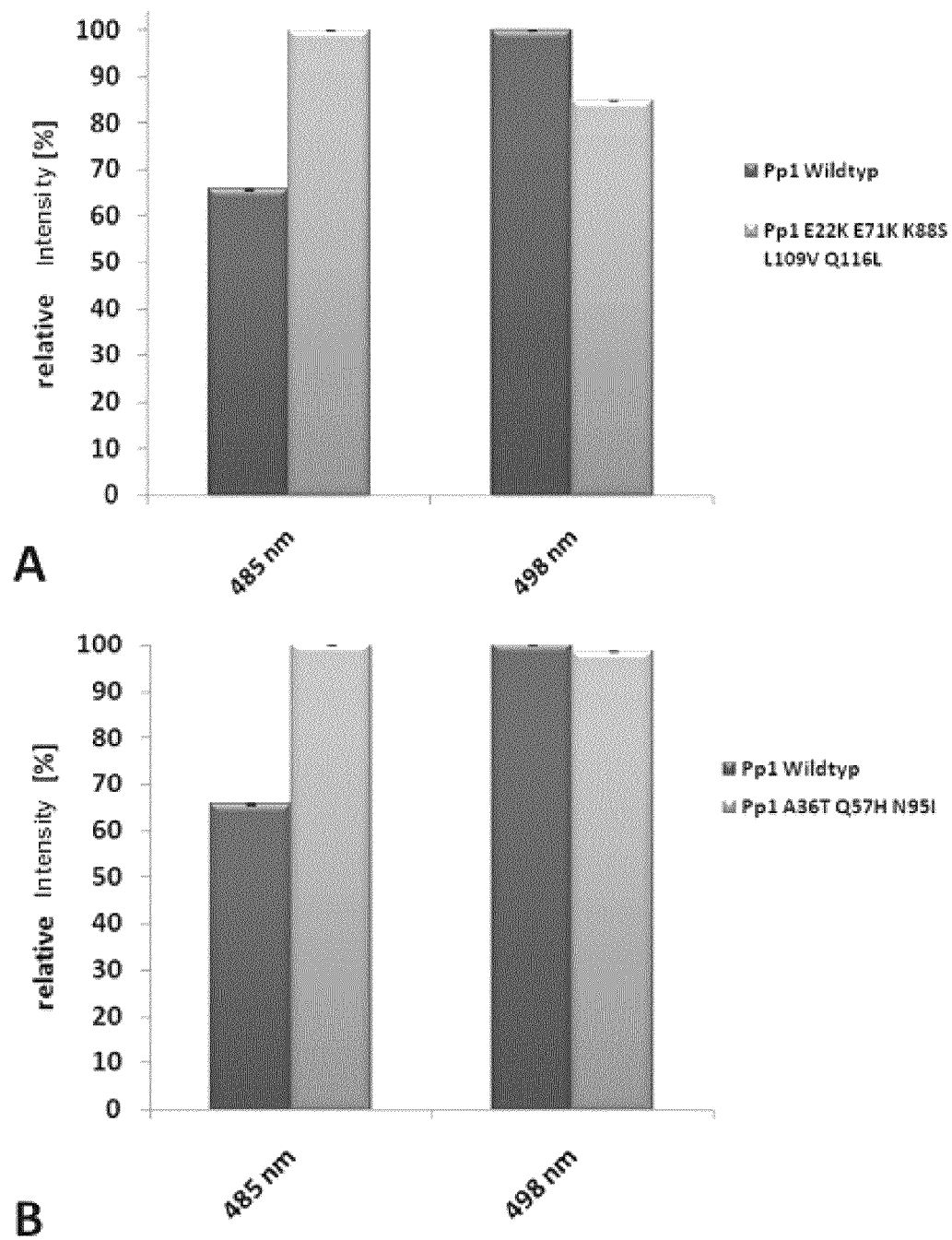

FIG. 4: Comparison of the relative intensities of Pp1 variants with shifted emission spectra with those of the wild type at the respective absolute maximums.

Figure 5:
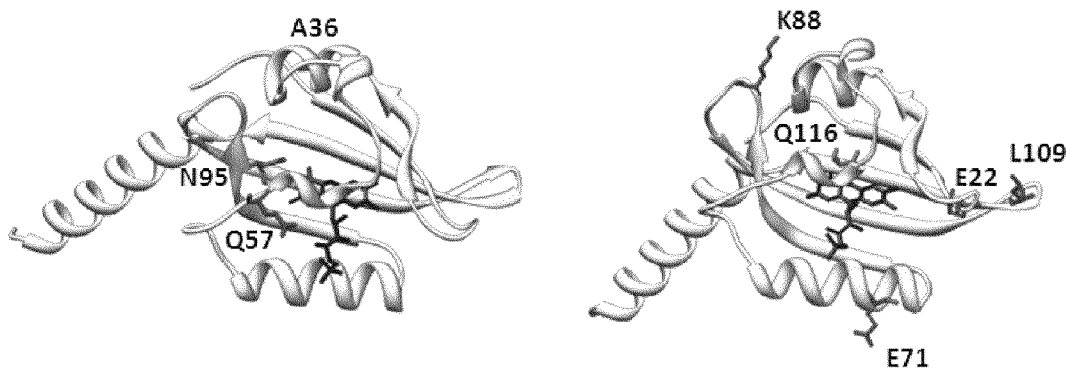

FIG. 5: Position of the mutagenized amino acids in the structure model of EVOGLOW®-Pp1 in variants, in which a color shift could be demonstrated. Dark gray accentuated amino acids (A36, N95, Q57, K88, Q116, E22, L109, E71) indicate the respective positions with identified substitutions. The structures were visualized with UCSF Chimera.

Figure 6:
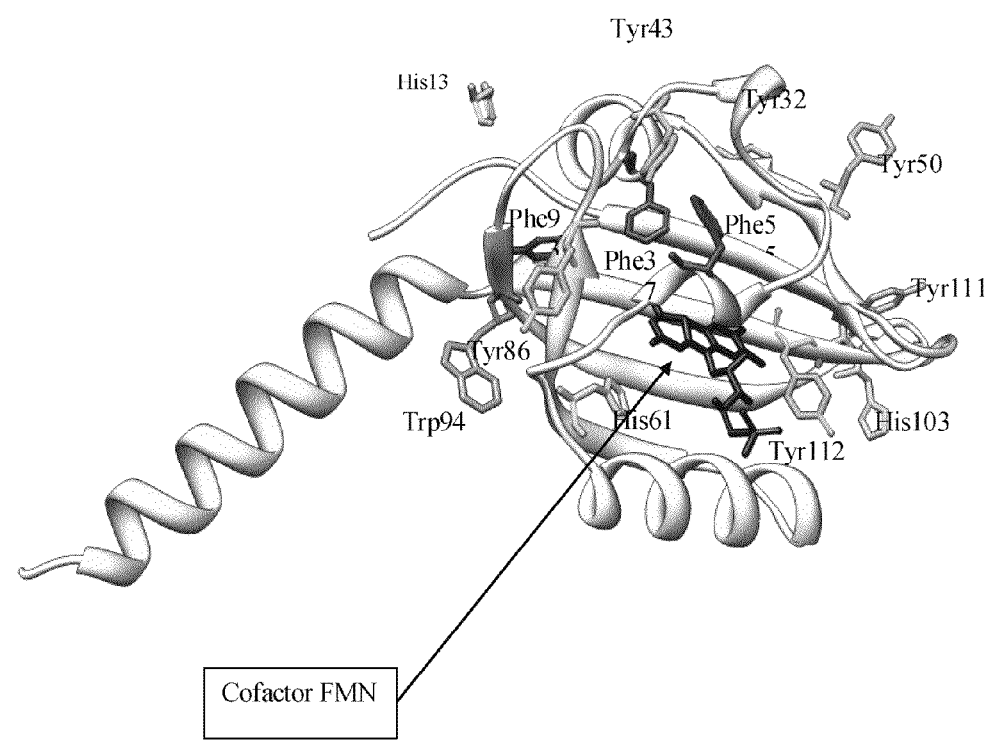

FIG. 6: Representation of all positions in the EVO-GLOW®-Pp1 structure model where Trp, Tyr, Phe or His is present. Cofactor FMN is shown in a central position in dark gray. The structure was visualized with UCSF Chimera.

FIG. 7: Dark and bright structures of YtvA from *B. subtilis* (PDB Codes: 2PR5 and 2PR6). The structure solved in darkness is represented in light gray, the one with illumination in cyan. The proteins are shown in ribbon representation. Cofactor FMN and residue F46 of YtvA corresponding to F37 are shown in stick mode.

FIG. 8: Alignment of the primary sequences of the fluorescent proteins EVOGLOW®-BsX (EVOGLOW®-Bs1 is SEQ ID NO:1; EVOGLOW®-Bs2 is SEQ ID NO: 2) and EVO-GLOW®-Pp1, which is SEQ ID NO: 4. The alignment was carried out with the ClustalW algorithm and displayed using BioEdit. The residues framed in blue and designated with F designate positions have so far been found in connection with wavelength of the emission, i.e., color variations of the fluorescent proteins and putatively entail them. The amino acids framed in red and designated with H show positions are thought to be associated with the change in fluorescence intensity. Thus, while not being bound to a particular theory, it is believed that the change of fluorescence intensity or color is not related to a specific amino acid but to a substitution at one or more of these specific positions.

FIG. 9: Interaction map of the protein moiety of YtvA with cofactor FMN. The involved atoms of the cofactor are given vertically; the amino acid residues of the protein are given horizontally. The type of interaction is indicated by the following symbols: hydrophobic interaction: Δ; hydrophilic interaction: O, H bridge:$^x$.

Figure 10:
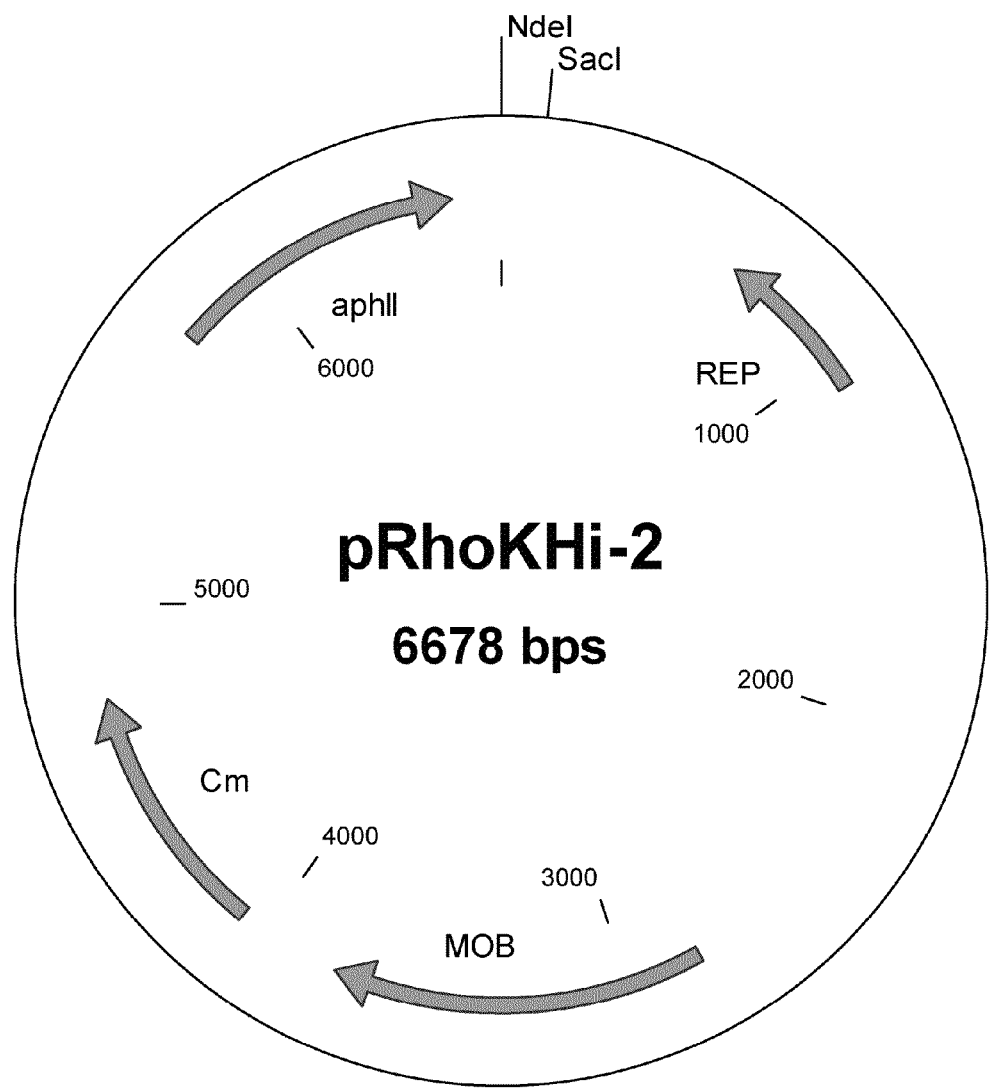

FIG. 10: Vector map of pRhoKHi-2.

DETAILED DESCRIPTION OF PREFERRED EMBODIMENTS

The present invention is directed to improved fluorescent proteins, which are based on modified blue light receptor proteins containing an LOV domain. Among the advantages of the fluorescent proteins (FPs) of the present invention is the provision of brighter FP variants with improved quantum yield and/or shifted excitation or emission spectrum. This allows for easier differentiation of cells in assay which utilize two or more different fluorescent proteins; however, the FPs of the present invention can also be used singly in any assay that uses a fluorescent protein. Furthermore, many of the commercially available fluorescent proteins require the presence of oxygen in order to generate fluorescence. In contrast, the FPs of the present invention can function in both aerobic and anaerobic biological systems, providing another advantage for their use.

In one embodiment of the present invention, the FP is isolated from *Bacillus subtilis* or from *Pseudomonas putida*, and modified as described herein. In a more preferred embodiment, the fluorescent protein of the present invention is obtained from *Pseudomonas putida* and modified in accordance with the present invention.

In an embodiment of the invention, the fluorescent protein comprises an LOV domain in which at least one cysteine is replaced by another amino acid that does not covalently bind FMN, and which besides the substitution of at least one cysteine comprises between 1 and 30, preferably between 1 and 20, and more preferably between 1 and 10 further point mutations which improve the fluorescence intensity, photostability and/or change the fluorescence wavelength of the fluorescent protein. In one preferred embodiment, the another amino acid which is used to replace cysteine is alanine.

It is another embodiment of the present invention to provide the LOV domain, which comprises at least one point mutation from the group consisting of I29V, S91G, Y112F, E138G, L7P, F124L, N26Y, Y112H, I48T, H61Y, Y43F, Y112C, E12D, Q143L, A36T, Q57H, N95I, E22K, E71G, K88S, L109V and Q116L, wherein the numbering is based on the wild-type Pp1 variant amino acid numbering. In one embodiment, the fluorescent protein of the present invention comprises a Y112H mutation in the LOV domain. In another embodiment, the FP of the present invention comprises a H61Y mutation, and in yet another embodiment, the FP comprises a N26Y mutation. In still another embodiment, the FP of the present invention comprises a D52 mutation in the LOV domain.

In a preferred embodiment of the invention, the LOV domain is an amino acid sequence in accordance with any one of sequences 1, 2, 3 or 4 comprising at least one additional point mutation, preferably between 1 and 30, more preferably between 1 and 20, and most preferably between 1 and 10 point mutations.

In another embodiment, the LOV domain of the present invention is encoded by a DNA sequence selected from the group of nucleic acid sequences 5, 6, 7, 8, 9, 10, 11, 12, 13 and 14.

In another embodiment, the fluorescent protein of the present invention has an LOV domain in which at least one cysteine is replaced by another amino acid that does not covalently bind FMN, characterized in that the LOV domain comprises besides the substitution of the at least one cysteine at least one further point mutation for improving the fluorescence intensity, photostability and/or for changing the fluorescence wavelength, and has an emission maximum that is shifted by at least 4 nm compared to a fluorescent protein with an LOV domain in which one cysteine is replaced by another amino acid that does not covalently bind FMN. In another embodiment, the fluorescent protein of the present invention has an emission maximum that is shifted by at least 10 nm compared to a fluorescent protein with an LOV domain in which one cysteine is replaced by another amino acid that does not covalently bind FMN. In the compared fluorescent protein, cysteine is preferably replaced with alanine. By way of example and not of limitation, the fluorescent protein of the present invention is compared to a protein having an amino acid sequence 1, 2, 3 or 4.

With respect to the DNA sequences of the FPs of the present invention, any DNA sequence encoding the fluorescent protein of the present invention can be used, with complimentary DNA (cDNA) sequences being preferred. It is another embodiment to provide FP nucleic acids that are codon optimized for expression in a particular organism. The term "codon optimized" is used herein to mean changes in the codons of the gene of interest to those preferentially used in a particular organism such that the gene is efficiently expressed in the organism. Although the genetic code is degenerate in that most amino acids are represented by several codons, it is well known that codon usage by particular organisms is non-random and biased towards particular codon triplets. Thus, changing the codons to the preferred codons of a particular organism may allow higher level expression of the encoded protein in that organism. In this regard, the present invention includes fluorescent protein variants whose codons are altered to the preferred codons of the organism in which the gene of interest is being expressed. In other words, codons are preferably selected to fit the host cell in which the protein is being produced. For example, preferred codons used in bacteria can be used to express the gene in bacteria; preferred codons used in yeast can be used for expression in yeast; and preferred codons used in mammalian cells can be used for expression in mammalian cells.

In another embodiment, the fluorescent proteins of the present invention include FPs containing codons replaced with degenerate codons coding for the same amino acid. This arises from the degeneracy of the genetic code where the same amino acids are encoded by alternative codons. Replacing one codon with another degenerate codon changes the nucleotide sequence without changing the amino acid residue. Thus, having identified a particular amino acid sequence, one skilled in the art could make any number of different nucleic acids by simply modifying the sequence of one or more codons in a way which does not change the amino acid sequence of the protein.

By way of example and not of limitation, suitable FPs of the present invention can be identified by screening gene libraries of randomly mutated flavin mononucleotide-based fluorescent proteins generated from blue-light photoreceptors from *Bacillus subtilis* and *Pseudomonas putida* that contain light-oxygen-voltage-sensing domains.

Figure 1A:
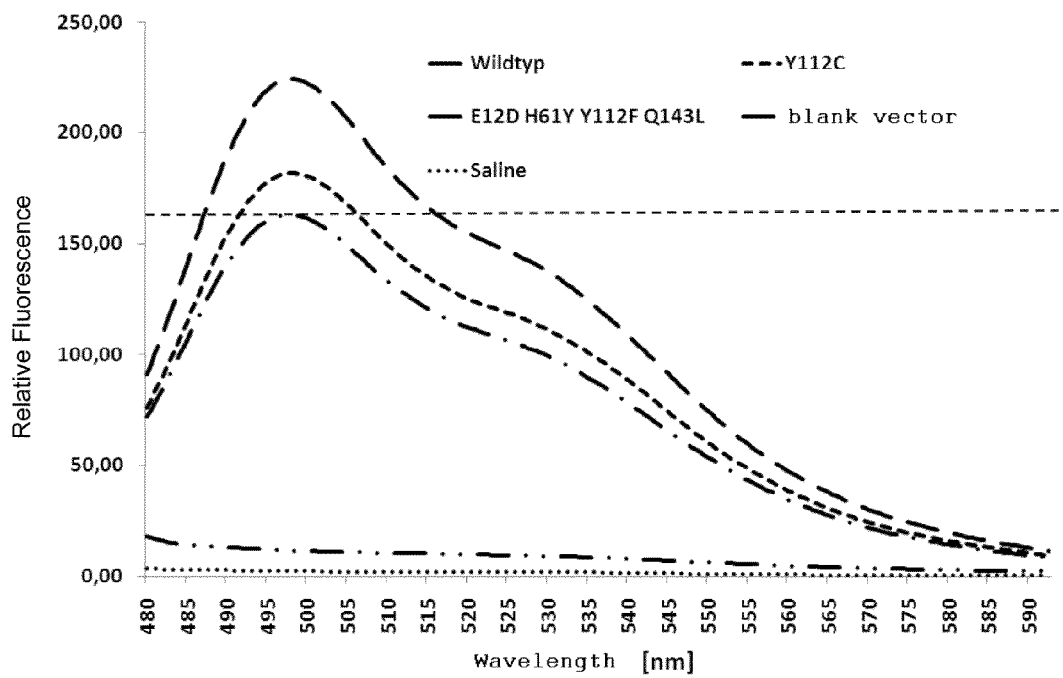
FIG. 1: (A) Emission fluorescence spectra of *E. coli* liquid cultures, which express the fluorescent marker EVOGLOW®-Pp1 or selected mutagenized variants. The cells were washed with saline and normalized to a cell density corresponding to an $O.D._{580\,nm}$ of 0.5. The emission spectrum was recorded at an excitation wavelength of 495 nm. (B) Summary of the change of the relative fluorescence intensity at the absolute maximum. The data was taken from the recorded fluorescence spectra.
Figure 1B:
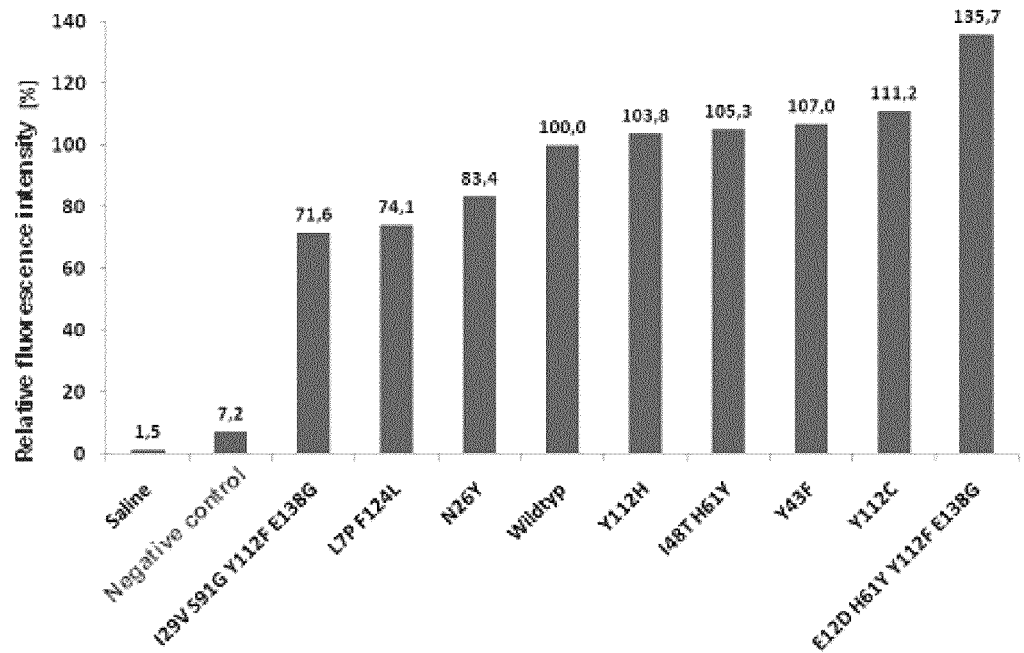
Figure 2:
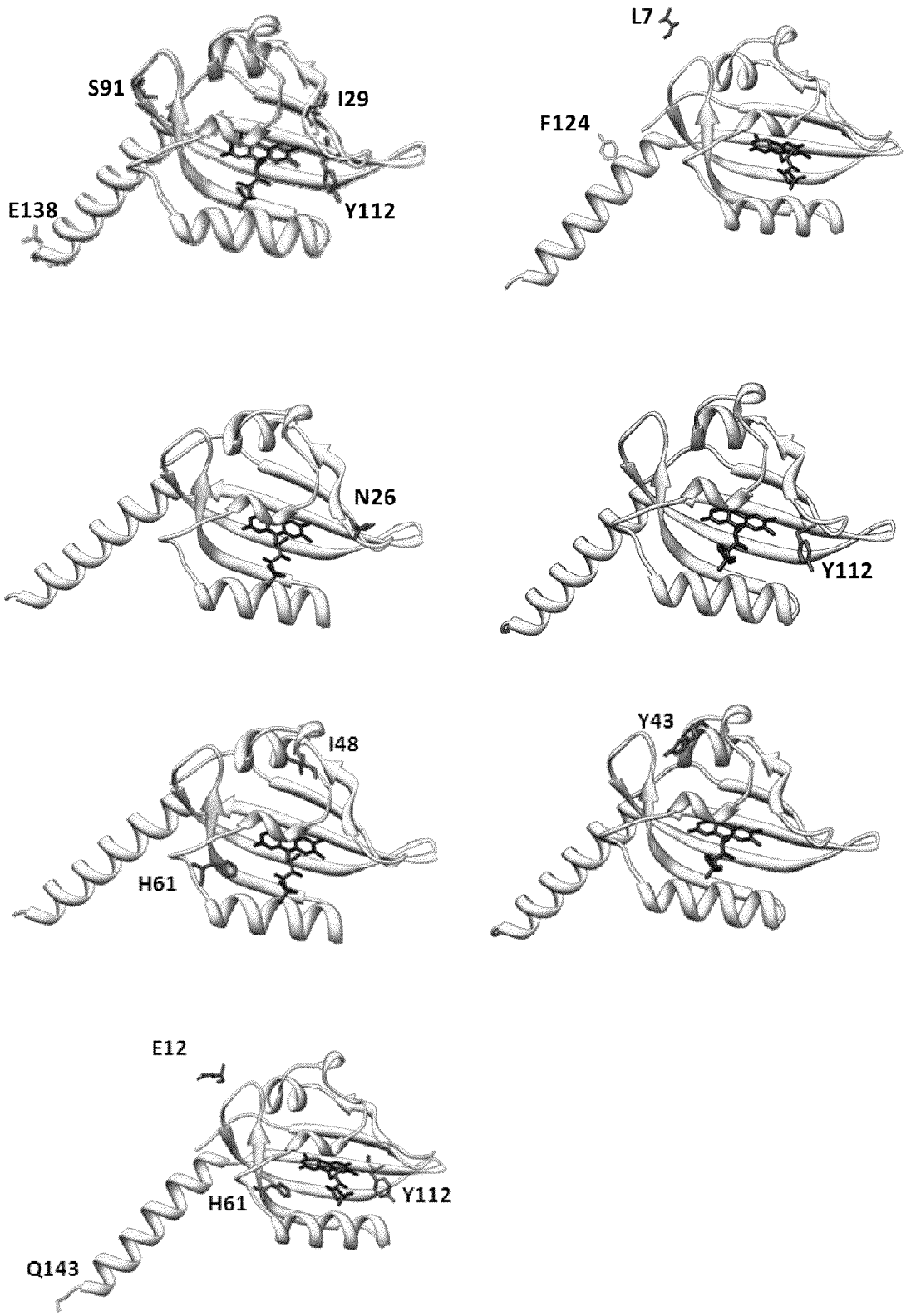
FIG. 2: Position of the mutagenized amino acids in the structure model of EVOGLOW®-Pp1 in variants, in which a change of brightness was detected. Amino acids shown in a darker shade of gray (S91, I29, Y112, L7, N26, H61, I48, Y43, E12) show respective positions with identified substitutions, some residues being taken from the homologous structure of YtvA since they were not calculated when the model of Pp1 was generated. In case of L7 the first amino acid (V11)

As an exemplary embodiment, a gene library was created by directed evolution using ep-PCR and introduction of random mutations into the gene coding for fluorescent marker EVOGLOW®-Pp1. Hereafter, this gene library was cloned into vector pRhoKHi and expressed in *E. coli* in order to be able to subsequently examine the variants of the fluorescent proteins for changes in the fluorescence properties. By this approach, different positions or mutations could be identified, which surprisingly caused a change in the fluorescence intensity (see FIG. 1 and Table 1).

A number of exemplary FP variants of the present invention are shown in Table 1 below.

TABLE 1

Identified protein variants of EVOGLOW ®-Pp1 and their brightness.

| Mutation | Rel. intensity to EVOGLOW ®-Pp1 | |
|---|---|---|
| | ImageJ | Fluorescence photometer |
| Pp1 Wild type | 100 ± 2 | 100% |
| I29V, S91G, Y112F, E138G | 19 ± 2 | 71.6% |
| L7P, F124L | 100 ± 8 | 74.1% |
| N26Y | 119 ± 2 | 83.4% |
| Y112H | 134 ± 9 | 103.8% |
| I48T, H61Y | 93 ± 2 | 105.3% |
| Y43F | 100 ± 7 | 107.0% |

TABLE 1-continued

Identified protein variants of EVOGLOW ®-Pp1 and their brightness.

| Mutation | Rel. intensity to EVOGLOW ®-Pp1 | |
|---|---|---|
| | ImageJ | Fluorescence photometer |
| Y112C | 118 ± 12 | 111.2% |
| E12D, H61Y, Y112F, Q143L | 153 ± 1 | 137.1% |

The relative intensity of the fluorescence emission was determined comparatively with the wild-type protein on the one hand with the aid of liquid cultures in computer-assisted fashion with image analysis software ImageJ and on the other hand spectrophotometrically in the fluorescence photometer. Data determined with ImageJ represent average values from two independently performed measurements.

In the course of the examination of the libraries, variants with both reduced and increased fluorescence emission could be identified. In the majority of these variants, some of the substitutions are located in direct spatial proximity to the cofactor and/or involve an aromatic amino acid residue, which due to the conjugated double bonds could absorb significant portions of the incident or emitted radiant energy (so-called quenching effect). Some of the mutagenized positions occur repeatedly, resulting in the so-called hot spots for mutations, which are summarized in Table 2.

TABLE 2

Frequency of mutations at selected positions in EVOGLOW ®-Pp1 with proven effect on the brightness of EVOGLOW ®-Pp1.

| Positions | Frequency with 10 variants |
|---|---|
| Y112H | 4 |
| H61Y | 2 |

Furthermore, two variants of EVOGLOW®-Pp1 with an emission spectrum that is shifted into the shorter wavelength range obtained by point mutations according to the invention were identified, which compared to the wild-type protein emitted a more bluish-green light (see Table 3 and FIGS. 3 and 4).

With both variants, the shift of the emission spectrum into the shorter wavelength range is accompanied by a reduction of the fluorescence intensity. While not being bound to a particular theory, the cause for this is believed to lie in the higher energy of the emitted light with a shorter wavelength. Table 3 provides a summary of the mutations, the relative intensity of the fluorescence and the shift of the emission maximum. The position of the introduced substitutions in the structure model of EVOGLOW®-Pp1 is shown in FIG. 5.

TABLE 3

Identified protein variants of EVOGLOW ®-Pp1 and their brightness and the shift of the emission maximum.

| Mutation | rel. intensity to EVOGLOW ®-Pp1 | | Shift of the emission maximum |
|---|---|---|---|
| | ImageJ | Fluorescence photometer | |
| A36T, Q57H, N95I | 60.5 ± 7 | 24.7% | −4 nm (494 nm) |
| E22K, E71G, K88S, L109V, Q116L | 109 ± 10 | 53.8% | −12 nm (486 nm) |

The relative intensity of the fluorescence emission was determined comparatively with the wild-type protein on the one hand with the aid of liquid cultures in computer-assisted fashion with ImageJ and on the other hand spectrophotometrically in the fluorescence photometer. The emission maximums were determined using the photometrically acquired spectra. Data determined using ImageJ represent average values from two independently performed measurements.

By means of the two protein variants just described, it could be shown that in principle it is possible to change the emission spectra of the EVOGLOW® proteins and hence the appearance in terms of color of the fluorescence reporters. In case of other fluorescence reporters such as the green fluorescent protein (GFP) and its derivatives this finding is fairly obvious since the fluorophore is formed by amino acid side chains, and mutagenesis of these amino acids contributing to maturation can therefore be utilized to generate new color variants. In case of EVOGLOW® proteins, however, the fluorophore is not provided by the protein moiety itself but rather by the so-called prosthetic group flavin mononucleotide (FMN) present in the protein. As a result, in contrast to GFP, the fluorescence behavior of the protein with respect to excitation and emission properties is mainly determined by the cofactor and not by the protein moiety itself. For this reason it is very surprising that it is possible to produce the fluorescence properties by changing the surrounding protein, and not the chromophore itself.

Both variants with shifted fluorescence spectrum comprise one or more mutations in direct spatial proximity to the cofactor. Here, the mutagenized amino acid residues Q57, N95 and Q116 all form direct ionic bonds with the cofactor and putatively contribute to its correct positioning. Without being bound to this theory, it is currently assumed that with these variants a slight shift of the cofactor in its bond cavity produces a changed fluorescence spectrum.

In connection with brighter variants of the fluorescence protein, surprisingly a great number of substitutions were identified where amino acids with side chains, which are located in the proximity of the chromophore and have aromatic structures or conjugated bonds, were involved. Based on these results, further residues potentially exerting influence were identified, which through their conjugated π-electrons could absorb energy in the form of radiation and hence are able to participate in quenching reactions that reduce the quantum yield and fluorescence intensity. A summary of these residues is given in FIG. 6 and Table 4.

TABLE 4

Summary of Trp, Tyr, Phe and His residues comprised in EVOGLOW ®-Pp1 and their distance to FMN.

| Residue | Distance to FMN (shortest distance/Å) |
|---|---|
| Phe37 | 3.803 |
| His61 | 3.835 |
| Tyr112 | 3.897 |
| Phe93 | 7.714 |
| Phe55 | 7.995 |
| Tyr86 | 8.141 |
| Tyr111 | 9.508 |
| Trp94 | 10.346 |
| Tyr32 | 11.363 |
| Tyr43 | 11.363 |
| His103 | 14.647 |
| Tyr50 | 14.929 |
| His13 | 18.885 |

The distance of the side chains was determined in each case as the shortest distance to FMN using UCSF Chimera and the structure model of EVOGLOW ®-Pp1.

It becomes apparent that mutation of residues His 61 and Tyr112 causes a change in the fluorescence behavior of the protein (see Table 1 and Table 2). In case of Phe37, in the analysis of the tertiary structures of YtvA it was noticed that distinct light-induced molecular motion occurs in the dark-bright transition (FIG. 7). Hence, mutagenesis of this residue is also a possibility to provide new fluorescent protein variants with modified brightnesses and/or fluorescence spectra.

Comparative alignment of the primary structures of EVOGLOW®-Bs (*Bacillus subtilis*) proteins with the amino acid sequence of EVOGLOW®-Pp1 (*Pseudomonas putida*) provides important data regarding the translatability of the obtained findings to other FMN-based fluorescence proteins (FIG. 8).

Some of the variants found in connection with reduced fluorescence intensity had only one substitution, which therefore obviously has a direct influence on the brightness. It is noticeable that precisely these mutagenized positions (D52G and N26Y) are not conserved in the alignment.

As already mentioned, in the course of the mutagenesis a surprisingly great number of improved variants were identified where a substitution of amino acids, which interact directly with the chromophore and are well conserved in the EVOGLOW® proteins, had taken place. Hence, it is the more unexpected that a substitution of these residues putatively essential for the function can have a positive influence on the fluorescence behavior.

Based on these surprising results, with the help of the solved structure of the YtvA protein, further amino acids were identified, which also interact directly with FMN and potentially exert significant influence on the fluorescence properties of the EVOGLOW® proteins.

A summary of the residues interacting with FMN and the type of interaction is given in FIG. 9.

From FIG. 9 and the alignment of the EVOGLOW® proteins (FIG. 8) the following positions result for the amino acids interacting with FMN in EVOGLOW®-Bs1 and -Bs2 and -Pp1 (see Table 5).

TABLE 5

Summary of the amino acid residues interacting with FMN in EVOGLOW ®-Bs1 and Bs2 and evoglow ®-Pp1.

| Type of interaction (Δ: hydrophobic; o: hydrophilic, x: H bridge) | Position in EVOGLOW ®-Bs1 and EVOGLOW ®-Bs2 | Homologous position in EVOGLOW ®-Pp1 |
|---|---|---|
| Δ, x | T30 | A21 |
| x | N37 | N35 |
| x | F46 | F37 |
| x | N61 | D52 |
| Δ, x | A62 | A53 |
| o, x | R63 | R54 |
| o, x | Q66 | Q57 |
| Δ, x | V75 | I66 |
| Δ, x, o | I78 | I69 |
| Δ, x | R79 | R70 |
| o, x | L82 | I73 |
| o, x | N94 | N85 |
| o, x | N104 | N95 |
| Δ, x | L106 | L97 |
| Δ | I108 | I99 |
| Δ, x | F119 | Y112 |
| Δ | V120 | I113 |
| Δ, x | G121 | G114 |
| o, x | Q123 | Q116 |

The positions were identified based on data from FIGS. 8 and 9.

The invention is also directed to a method for producing a fluorescent protein of the present invention, wherein a plasmid comprising a DNA sequence encoding the fluorescent protein is introduced by means of genetic engineering methods into an organism, for example a bacterium selected from the group consisting of *Escherichia coli, Rhodobacter capsulatus, Pseudomonas putida* and *Bacillus subtilis* and is expressed therein. In one preferred embodiment, cDNA sequences of the fluorescent proteins of the present invention are used for their expression. One of ordinary skill in the art can determine optimal conditions for expressing an FP of the present invention without undue experimentation by altering factors such as media components, temperature, cell density and the like. The expressed FP is next purified according to the standard protocols used in the art. Such methods include affinity chromatography, ultracentrifugation, size exclusion chromatography, ion exchange chromatography and electrophoresis techniques.

The invention is also directed to the use of a fluorescent protein as a fluorescent marker, in particular in solutions or cells, wherein the fluorescent protein has an LOV domain in which at least one cysteine is replaced by another amino acid that does not covalently bind FMN, characterized in that the LOV domain comprises besides the substitution of the at least one cysteine at least one further point mutation for improving the fluorescence intensity, photostability and/or for changing the fluorescence wavelength. As is well known in the art, fluorescent proteins can be used as biological markers for cellular processes such as gene expression, protein targeting (intracellular trafficking and localization), protein interactions, and biosensors technologies. In addition, the lack of oxygen requirement makes the fluorescent proteins of the present invention useful for high-throughput screening for anaerobic bacteria, and the development of cancer therapies involving the use of anaerobic bacteria as anti-tumor agents. For a majority of applications, the fluorescent protein of the present invention is linked to a protein of interest.

Methods for generating chimeric FP fusion proteins are well known in the art. Briefly, the methods include linking DNA encoding a gene of interest, or portion thereof, to DNA encoding a FP coding region in the same translational reading frame. The encoded-protein of interest may be linked in-frame to the amino- or carboxyl-terminus of the FP. The DNA encoding the chimeric protein is then linked in operable association with a promoter element of a suitable expression vector. Alternatively, the promoter element can be obtained directly from the targeted gene of interest and the promoter-containing fragment linked upstream of the FP coding sequence to produce chimeric FP proteins. The nucleic acid encoding the chimeric FP protein is next inserted into a host organism and expressed therein.

In a number of embodiments, the FP fusion proteins (fluorescent proteins of the present invention operably linked to a protein of interest) are used for tracking or localizing the protein to a particular subcellular location, quantitating gene expression, display of peptides, indicating a cellular reaction, or as markers for cell growth and proliferation.

In one embodiment, the FP fusion protein according to the present invention can be used to track and localize proteins intracellularly or extracellularly. Fusion may be made to any protein of interest to examine cellular processing events of the protein. Proteins of interest include, but are not limited to, cytoskeletal proteins for tracking cell movement and cell structure; focal adhesion proteins involved in cell adherence; nuclear proteins for examining signals involved in nuclear transport; and nuclear membrane proteins involved in nuclear membrane dissolution and reformation, cell organelle replication and structure, intracellular transport of proteins (e.g. targeting signals), development of structural polarity in cells (e.g., neuronal or epithelial cells), monitoring cell division processes, and the like. Many of these aforementioned processes are abnormal in diseased cells, such as cancer cells. Accordingly, these fusion proteins, when expressed in diseased cells, such as cancer cells, are useful for identifying candidate agents that affect these biological processes in particular cell types. Thus, screens can be conducted for agents that confer a phenotype similar to a disease cell or for agents that convert an abnormal cell, characterized by an abnormal cellular process, to a normal cell.

Generally, for these processes, following the generation of the nucleic acid encoding the fusion product of FP of the present invention and a protein of interest, a vector containing such nucleic acid is transfected into cells to be studied. In one embodiment, the vector is a plasmid. A plasmid vector is selected in part based upon the host cell that is to be transformed with the plasmid. For example, the presence of bacterial or mammalian selectable markers present in the plasmid, the origin of replication, plasmid copy number, an ability to direct random or site specific recombination with chromosomal DNA, etc. can influence the choice of an appropriate vector. In another embodiment, the vector is a virus. The viruses useful in the practice of the present invention include recombinantly modified enveloped or non-enveloped DNA and RNA viruses, preferably selected from the baculoviridiae, parvoviridiae, picornoviridiae, herpesviridiae, poxyiridiae, and adenoviridiae viruses. In some embodiments, the recombinant virus is a baculoviridiae virus. A number of different plasmids and viruses, which can be used as vectors are well known in the art.

Cells to be studied can be, for example, bacterial cells, yeast cells, and mammalian cells. A mammalian cell can be a mammalian cell that is isolated from an animal (i.e., a primary cell) or a mammalian cell line. Methods for cell isolation from animals are well known in the art. Furthermore, host cell lines are typically available from, for example, the American Tissue Culture Collection (ATCC), any approved Budapest treaty site or other biological depository.

After transfection into host cells, the fusion FP protein is expressed based on the expression of the protein of interest, which forms a part of the FP fusion protein. Thus, the FP of the present invention is expressed in the same location and amount as the protein of interest, and will be affected by factors that affect the protein of interest. Thus, the readout of fluorescence of the FP in the host cells provides information regarding the role of the protein of interest in the host cells. Any of the standardly used methods in the art for fluorescence readout can be used, such as spectrometry or fluorescence microscopy. By way of example and not of limitation, fluorescence microscopy can be used to determine a protein's cellular location or to follow cellular trafficking. Similarly, spectrometry can be used to, e.g., quantitate gene expression.

As mentioned above, the fluorescent proteins of the present invention can be used as part of biosensor systems. In one embodiment, a nucleic acid encoding the FP of the present invention is operably linked to a promoter, i.e. an inducible promoter, which is expressed only in the presence of certain factors or compounds. After inserting the nucleic construct encoding for such promoter and FP of the present invention into host cells, the FP will be expressed only if factor(s)/compound(s), which are needed for promoter activation are present in the host cells and/or media containing them. Thus, expression of the FP fluorescence, measured by any of the methods discussed above, can be used to sense the presence of factors or compounds being tested. Alternatively, methods such as the one described by Doi and Yanagawa (FEBS Letters, Volume 453, Issue 3, pages 305-307, June 1999), which is incorporated herein by reference, can be used. Briefly, as the first step, a protein domain containing a desired molecular-binding site is inserted into a surface loop of the fluorescent protein. Next, the insertional fusion protein is randomly mutated, and new allosteric proteins that undergo changes in fluorescence upon binding of target molecules are selected from the random library. These allosteric proteins can then be inserted into cells and used to sense certain compounds based on their molecular-binding site. The change in fluorescence, which can be measured by any standard methods in the art, can be used to indicate presence of such compounds in cells or media.

Additionally, the fluorescent proteins of the present invention can be used for high-throughput screening of anaerobic and aerobic cell cultures. Prior to growing the cultures, cells are transfected with vectors comprising a fluorescent protein described herein. The expression of the fluorescent protein in the cultures can be used to monitor cell growth, e.g., by fluorescence spectrometry.

In another embodiment, the FP fusion proteins described herein are useful in marking viruses and cells, and as reporters for cell proliferation. Briefly, general expression or specific regulated expression of the FP fusion proteins marks the cell or a virus, either constitutively or at specific periods in development. This can be achieved by inserting a nucleic construct coding for the FP fusion protein into host cells or viruses either under the control of a constitutive promoter or an inducible promoter. These marked viruses or cells may be detected and tracked by e.g., spectrometry or fluorescence microscopy to determine their migration or proliferation in an organism or in response to specific biological signals, for example cytokines and chemokines. Furthermore, these cells may be used in screens to identify candidate agents that alter the infectivity, migration or proliferation of these viruses or cells in response to the biological signals by comparing the fluorescence readout of cells before contacting them with candidate agents and after such contact.

In another embodiment, FP fusion proteins can be used to scan a host chromosome for promoter elements. Briefly, the fusion nucleic acids encoding an FP of the present invention and a weak promoter, or no promoter, are inserted into a host chromosome. In a preferred embodiment, this may be done conveniently by using a viral backbone for constructing the fusion nucleic acids. For example, in bacteria, the phage Mu systems allow random insertions into the host chromosome while in mammalian cells, retroviral vectors provide a suitable vehicle for inserting the fusion nucleic acids into the host chromosome. When retroviral vectors are used, SIN type vectors lacking viral promoters are preferred so that the reporter gene is transcribed or activated from endogenous promoters or promoter regulatory elements upon insertion of the viral DNA into the host chromosome. Expression of the fluorescent protein indicates insertion near an endogenous promoter. Identifying cells expressing the reporter gene upon treatment with inducers allow identification of promoters regulated by the inducing agent. Cells comprising these insertions are contacted with candidate agents, for example, by expressing candidate nucleic acid or proteins in the cells. Those agents modulating promoter activity are identified based on expression of the fluorescent protein reporter, e.g., by spectrometry or fluorescence microscopy.

In still another embodiment, the fluorescent proteins of the present invention are useful in identifying candidate agents that bind specific cells, tissues or organs. Cells expressing libraries of candidate agents comprising a fluorescent protein described herein are contacted with cells or introduced into an organism, and candidate agents that bind to specific cells are selected by standard methods in the art. These bioactive candidate agents can be useful for targeting antibodies, enzymes, drugs, or imaging agents coupled thereto to particular cells, tissues or organs. Coupling can be achieved either by expression of nucleic constructs coding for fusions of FP and antibody or enzyme, or by covalent bonding of the FP with any of the targeting agents. Methods for coupling reagents are standard in the art.

It is another embodiment of the present invention to provide kits directed to the use of the fluorescent proteins of the present invention. Briefly, the kit of the present invention can contain a plasmid and instructions for use, wherein the plasmid contains a nucleic acid sequence encoding a fluorescent protein of the present invention. In one embodiment, the plasmid contains a fluorescent protein as described herein, which comprises at least one point mutation from the group consisting of I29V, S91G, Y112F, E138G, L7P, F124L, N26Y, Y112H, I48T, H61Y, Y43F, Y112C, E12D, Q143L, A36T, Q57H, N95I, E22K, E71G, K88S, L109V and Q116L in the LOV domain, wherein the numbering is based on the wild-type Pp1 variant amino acid numbering. Additionally, the plasmid can contain multiple cloning sites (MCS) for production of a FP fusion protein.

Molecular biological techniques, biochemical techniques, and microorganism techniques as used herein are well known in the art and commonly used, and are described in, for example, Sambrook J. et al. (1989), Molecular Cloning: A Laboratory Manual, Cold Spring Harbor and its 3rd Ed. (2001); Ausubel, F. M. (1987), Current Protocols in Molecular Biology, Greene Pub. Associates and Wiley-interscience; Ausubel, F. M. (1989), Short Protocols in Molecular Biology: A Compendium of Methods from Current Protocols in Molecular Biology, Greene Pub. Associates and Wiley-interscience; Innis, M. A. (1990), PCR Protocols: A Guide to Methods and Applications, Academic Press; Ausubel, F. M. (1992), Short Protocols in Molecular Biology: A Compendium of Methods from Current Protocols in Molecular Biology, Greene Pub. Associates; Ausubel, F. M. (1995), Short Protocols in Molecular Biology: A Compendium of Methods from Current Protocols in Molecular Biology, Greene Pub. Associates; Innis, M. A. et al. (1995), PCR Strategies, Academic Press; Ausubel, F. M. (1999), Short Protocols in Molecular Biology: A Compendium of Methods from Current Protocols in Molecular Biology, Wiley, and annual updates; Sninsky, J. J. et al. (1999), PCR Applications: Protocols for Functional Genomics, Academic Press; Special issue, and the like. Relevant portions (or possibly the entirety) of each of these publications are herein incorporated by reference.

EXAMPLES

Example 1

Generating the Mutagenesis Library of the Genes Coding for the Fluorescent Proteins Mutagenesis of the genes coding for the fluorescence reporters occurred by error prone PCR. For this, random point mutations were introduced into the wild-type gene by utilizing Taq polymerase and further additives such as $MnCl_2$ and unphysiologically high concentrations of $MgCl_2$. The primers were chosen in such as way that they flanked the gene and added recognition sequences for the restriction enzymes Nde1 and Sac1 into the PCR products.

Example 2

Cloning the Library

The resulting ep-PCR products were cloned into vector pRhoKHi-2 (FIG. 10) by ligation. For this purpose, both the vector and the PCR products were hydrolyzed with the restriction endonucleases Nde1 and Sac1. After inactivation of the enzymes the vectors were ligated with the PCR products and competent E. coli DH5α cells were transformed with them.

Example 3

Screening the Libraries for Improved Variants

The screening for improved protein variants with regard to their brightness was performed with the help of a UV cabinet (Camag). The resulting transformants were photographed with a digital camera directly on the LB agar plate in the blue light box with excitation at a wavelength of 366 nm. Analysis of the brightness of the colonies on the plate occurred based on these pictures with the program ImageJ and the plug-in "3D Surface Plot". This plug-in allows for the visualization of brightnesses of a picture as a graphic representation of height topologies.

The determination of the color of the cultures also occurred in computer-assisted fashion with the program ImageJ after documentation of the colonies with a digital camera. For this purpose, the plug-in "3D Color Inspector" was used, which allows for the visualization of the color distributions of a picture in three-dimensional space.

Example 4

Measuring the Fluorescence of Liquid Cultures

Potentially brighter clones were grown again as liquid culture together with a culture, which carried a plasmid with the non-mutagenized fluorescence reporter, and incubated overnight at 37° C. and shaker speeds of 180 rpm. Afterwards, $O.D._{580\ nm}$ of the cultures was determined, and the cells were sedimented by centrifugation at 8000 g for 5 min. The resulting cell pellet was washed once with saline and subsequently resuspended in a volume of saline so that a $O.D._{580\ nm}$ of 25 was achieved. 10 μl each of these samples and a dilution series in 1 to 10 dilutions were transferred onto a Plexiglas plate and documented with the help of the blue light box and a digital camera. Analysis of the pictures occurred with ImageJ and the plug-in "3D Surface Plot" as described above, the culture, which expressed the non-mutagenized fluorescence reporter, being used as reference.

Example 5

Taking the Fluorescence Spectra of Liquid Cultures

Fluorescence measurements of whole cells were performed in 100 mM Tris-HCl pH 7.0. For this purpose, aliquotes corresponding to $O.D._{580\ nm}=1$ were taken from the respective expression cultures, pelletized (3 min, 8000 rpm, room temperature), and washed with 100 mM Tris-HCl pH 7.0. Subsequently, the cell suspension was adjusted with saline to a cell density corresponding to an $O.D._{580\ nm}$ of 0.5. The fluorescence of the samples was measured with a fluorescence photometer (Luminescence Spectrometer LS 506, Perkin Elmer, Boston, USA).

What is claimed is:

1. A recombinant fluorescent protein having a light, oxygen, voltage domain (LOV domain) in which at least one cysteine is replaced by another amino acid that does not covalently bind FMN, characterized in that the LOV domain is an amino acid sequence selected from the group consisting of SEQ ID NO: 1, 2, 3 or 4, wherein the LOV domain comprises the substitution of the at least one cysteine and at least one further point mutation for changing the fluorescence wavelength, selected from the group consisting of Y112H, I48T, H61Y, Y43F, Y112C, E12D, Q143L, A36T, Q57H, N95I, E22K, E71G, K88S, L109V and Q116L, and wherein the numbering of said point mutation is based on the amino acid sequence of SEQ ID NO: 4.

2. The fluorescent protein according to claim 1 wherein said another amino acid is alanine.

3. The fluorescent protein according to claim 1 having an emission maximum that is shifted by at least 4 nm compared to a fluorescent protein selected from the group consisting of amino acid sequences of SEQ ID NOs: 1, 2, 3 and 4.

4. The fluorescent protein according to claim 1 having an emission maximum that is shifted by at least 10 nm compared to a fluorescent protein selected from the group consisting of amino acid sequences of SEQ ID NOs: 1, 2, 3 and 4.

5. An isolated recombinant light, oxygen, voltage domain (LOV domain in which at least one cysteine is replaced by another amino acid that does not covalently bind FMN, characterized in that the LOV domain is an amino acid sequence selected from the group consisting of SEQ ID NO: 1, 2, 3 or 4, wherein the LOV domain comprises the substitution of the at least one cysteine and at least one further point mutation for changing the fluorescence wavelength selected from the group consisting of Y112H, I48T, H61Y, Y43F, Y112C, E12D, Q143L, A36T, Q57H, N95I, E22K, E71G, K88S, L109V and Q116L, and wherein the numbering of said point mutation is based on the amino acid sequence of SEQ ID NO: 4.

6. The LOV domain according to claim 5 wherein said another amino acid is alanine.

7. The LOV domain according to claim 6, said LOV domain being encoded by a DNA sequence in accordance with any one of the nucleotide sequences of SEQ ID NOs: 5 to 14.

* * * * *